(12) United States Patent
Song

(10) Patent No.: US 9,597,020 B2
(45) Date of Patent: Mar. 21, 2017

(54) MEASURING DEVICE AND GLUCOSE CONCENTRATION MEASUREMENT METHOD OF THE MEASURING DEVICE

(71) Applicant: ELECTRONICS AND TELECOMMUNICATIONS RESEARCH INSTITUTE, Daejeon (KR)

(72) Inventor: Hyun Woo Song, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 508 days.

(21) Appl. No.: 14/055,713

(22) Filed: Oct. 16, 2013

(65) Prior Publication Data
US 2014/0107438 A1   Apr. 17, 2014

(30) Foreign Application Priority Data

Oct. 16, 2012 (KR) .......... 10-2012-0115021
Jul. 2, 2013 (KR) .......... 10-2013-0076999

(51) Int. Cl.
*A61B 5/145* (2006.01)
*A61B 3/10* (2006.01)
(Continued)

(52) U.S. Cl.
CPC ........ *A61B 5/14532* (2013.01); *A61B 5/0066* (2013.01); *A61B 5/1455* (2013.01);
(Continued)

(58) Field of Classification Search
CPC .............. A61B 5/14532; A61B 5/1455; A61B 5/14558; A61B 5/0002; A61B 5/14555
See application file for complete search history.

(56) References Cited

U.S. PATENT DOCUMENTS 5,535,743 A * 7/1996 Backhaus ............... A61B 3/10
600/310
7,822,452 B2   10/2010 Schurman et al.
(Continued)

FOREIGN PATENT DOCUMENTS

JP   2009-136541 A   6/2009
JP   2011-511694 A   4/2011

OTHER PUBLICATIONS

Georgeanne Purvinis et al., "Noninvasive Polarimetric-Based Glucose Monitoring: An in Vivo Study", Journal of Diabetes Science and Technology, Mar. 2011, pp. 380-387, vol. 5, Issue 2, 2011 Diabetes Technology Society.
(Continued)

*Primary Examiner* — Tse Chen
*Assistant Examiner* — Yoojin Lee

(57) ABSTRACT

The inventive concept relates to a measuring device. The measuring device irradiates a first beam including a polarization component and a second beam which is a wavelength swept laser having a coherence length previously set and can measure a glucose concentration of an aqueous humor by measuring an optical path length and the rotation amount of a polarization plane respectively from a first output beam and a second output beam being output from an eye.

7 Claims, 6 Drawing Sheets

(51) Int. Cl.
*A61B 5/1455* (2006.01)
*A61B 5/00* (2006.01)

(52) U.S. Cl.
CPC .......... *A61B 5/14558* (2013.01); *A61B 3/102* (2013.01); *A61B 3/1005* (2013.01)

(56) References Cited

U.S. PATENT DOCUMENTS

| | | | |
|---|---|---|---|
| 8,180,422 B2 | 5/2012 | Rebec | |
| 8,219,169 B2 | 7/2012 | Gerlitz | |
| 2003/0233036 A1* | 12/2003 | Ansari | A61B 5/14558 600/316 |
| 2008/0119701 A1* | 5/2008 | Milner | A61B 5/0066 600/342 |
| 2012/0215079 A1* | 8/2012 | Cornsweet | A61B 5/14507 600/319 |

OTHER PUBLICATIONS

V. Jayaraman et al., "OCT Imaging up to 760 kHz Axial Scan Rate Using Single-Mode 1310nm MEMS-Tunable VCSELs with >100nm Tuning Range", 2011 Conference on Lasers and Electro-Optics (CLEO), May 1-6, 2011, pp. 1-2, Optical Society of America, Baltimore, USA.

\* cited by examiner

MEASURING DEVICE AND GLUCOSE CONCENTRATION MEASUREMENT METHOD OF THE MEASURING DEVICE

CROSS-REFERENCE TO RELATED APPLICATIONS

This U.S. non-provisional patent application claims priority under 35 U.S.C. §119 of Korean Patent Application No. 10-2013-0076999 and No. 10-2012-0115021, respectively filed on Jul. 2, 2013 and Oct. 16, 2012, the entire contents of which are hereby incorporated by reference.

BACKGROUND OF THE INVENTION

The present inventive concept herein relates to measuring devices, and more particularly, to a measuring device for measuring a glucose concentration of an aqueous humor in an anterior chamber of an eye and a glucose concentration measurement method of the measuring device.

Generally, there is a technology of non-invasively measuring a concentration not to cause pain to life forms such as humans, animals, etc. There are various technologies of non-invasively measuring a concentration.

For example, to measure a glucose concentration of an aqueous humor of a rabbit, a method has been suggested which measures a glucose concentration by comparing a blood glucose level with a glucose level of an aqueous humor of an eye.

However, an optical path entering an eye which moves very actively like an eye is difficult to be maintained constant. In the case that an optical path is not maintained constant, there is a problem not to accurately measure a concentration of a medium having a characteristic like an aqueous humor.

SUMMARY

Embodiments of the inventive concept provide a measuring device. The measuring device may include a beam generation unit generating a first beam including a polarization component and a second beam which is a wavelength swept laser having a coherence length previously set; a beam output unit sending a mixed beam obtained by mixing the first and second beams to an eye and receiving a first output beam returning from an eye in a first direction; a beam interference unit making interference between a first output beam and a reflection beam that is reflected from a reference reflector; an interference signal collection unit collecting an interference signal according to the interference; an optical activity measurement unit receiving a second output beam being output in a second direction having a specific angle with respect to the first direction to measure the rotation amount of a polarization plane; and a concentration measurement unit measuring an optical path length in the eye on the basis of the interference signal and measuring a glucose concentration of the eye on the basis of the optical path length and the rotation amount of a polarization plane.

Embodiments of the inventive concept also provide a method of measuring a glucose concentration of a measuring device. The method of measuring a glucose concentration of a measuring device may include generating a first beam including a polarizing component; generating a second beam which is a wavelength swept laser having a coherence length previously set; sending a mixed beam obtained by mixing the first and second beams to an eye in a first direction; measuring a net optical path length by interference between a reflection beam which is reflected from a reference reflector and a first output beam being output from the eye in a first direction; measuring the rotation amount of a polarization plane from a second output beam being output in a second direction having a specific angle with respect to the first direction; and measuring a glucose concentration of an aqueous humor on the basis of the net optical path length and the rotation amount of a polarization plane.

BRIEF DESCRIPTION OF THE FIGURES

Preferred embodiments of the inventive concept will be described below in more detail with reference to the accompanying drawings. The embodiments of the inventive concept may, however, be embodied in different forms and should not be constructed as limited to the embodiments set forth herein. Rather, these embodiments are provided so that this disclosure will be thorough and complete, and will fully convey the scope of the inventive concept to those skilled in the art. Like numbers refer to like elements throughout.

DETAILED DESCRIPTION OF PREFERRED EMBODIMENTS

Figure 1:
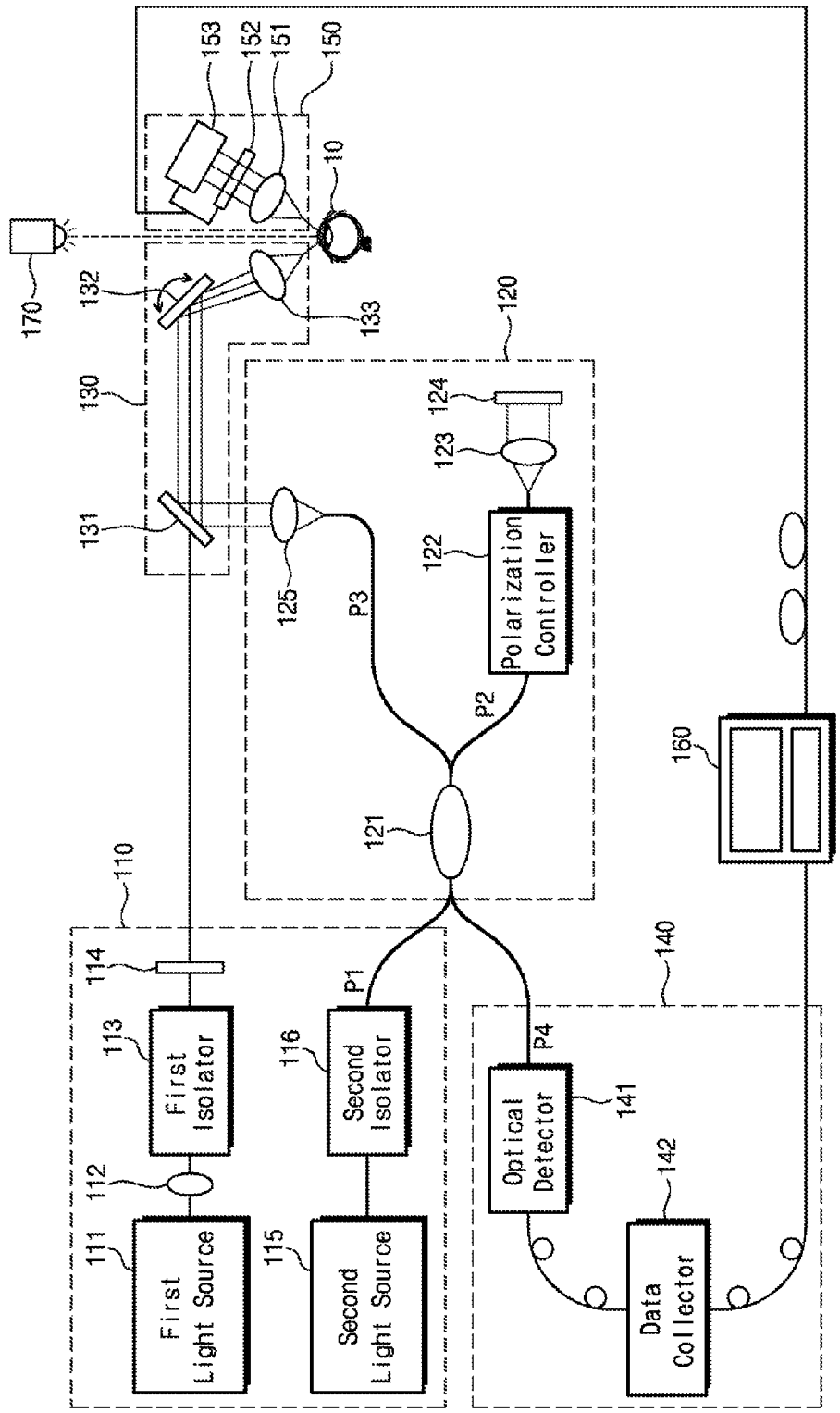
FIG. 1 is a drawing illustrating a measuring device according to some exemplary embodiments of the inventive concept.

Embodiments of inventive concepts will be described more fully hereinafter with reference to the accompanying drawings, in which embodiments of the invention are shown. This inventive concept may, however, be embodied in many different forms and should not be construed as limited to the embodiments set forth herein. Rather, these embodiments are provided so that this disclosure will be thorough and complete, and will fully convey the scope of the inventive concept to those skilled in the art. In the drawings, the size and relative sizes of layers and regions may be exaggerated for clarity. Like numbers refer to like elements throughout.

The inventive concept provides a measuring device non-invasively and accurately measuring a concentration of a medium having a characteristic like an aqueous humor of human or animal, for example, a glucose concentration. The measuring device of the inventive concept measures a glucose concentration of an aqueous humor contained in an anterior chamber between a cornea and a lens of an eye using an optical method. Thus, this measuring device can non-invasively measure a glucose concentration of aqueous humor.

FIG. 1 is a drawing illustrating a measuring device according to some exemplary embodiments of the inventive concept.

Referring to FIG. 1, a measuring device 100 includes a beam generation unit 110, a beam interference unit 120, a beam output unit 130, an interference signal collection unit 140, an optical activity measurement unit 150 and a concentration measurement unit 160.

A beam generation unit 110 generates a beam and outputs the generated beam to the beam interference unit 120 and the beam output unit 130.

The beam generation unit 110 includes a first light source 111, a first lens 112, a first isolator 113, a polarizer 114, a second light source 115 and a second isolator 116.

The first light source 111 generates a first beam. The first beam enters an anterior chamber of an eye. The first light source 111 outputs the generated first beam to the first lens 112.

The first lens 112 controls the first beam to output it to the first isolator 113.

The first isolator 113 outputs the first beam to the polarizer 114. The first isolator 113 blocks out an incoming light from the beam output unit 130.

The polarizer 114 applies polarization components to the first beam to output the first beam to the beam output unit 130. Thus, the first beam includes polarization components.

The measuring device 100 measures a concentration of aqueous humor in an anterior chamber of an eye 10 through a reflection of the first beam. To maximize the rotation amount of a polarized light reflected from the eye 10, the first beam generator 111 should use a beam having a short peak wavelength. However, since a wavelength of an ultraviolet region may damage an eye and has a low penetration depth. Thus, the first light source 111 may generate a beam of a visible light region when generating the first beam.

The first light source 111 can use a He—Ne laser, a semiconductor laser (a wavelength of 450 nm~780 nm) or a light emitting diode (LED) to generate the first beam.

The second light source 115 generates a second beam. The second beam is a wavelength swept laser having a wide bandwidth. The second beam has a good coherence, that is, a long coherence length (e.g., more than 10 mm).

The second beam can give a tomographic image for an anterior chamber of an eye. The second beam has a wavelength sweeping speed of more than several kilohertz in order to obtain a tomographic image in real time without a motion artifact.

A wavelength swept surface emitting laser or a serially connected module of a wavelength swept surface emitting laser and an optical amplifier may be used as the second light source 115. The second light source 115 can generate a second beam having a peak wavelength of an infrared region. For example, the second light source 115 can generate a second beam having a peak wavelength in the vicinity of 850 nm, 980 nm and 1300 nm.

Thus, the second light source 115 can sweep a wavelength of a beam being generated to obtain an interference light intensity distribution of depth direction of the eye 10. The second light source 115 outputs the generated second beam to the second isolator 116.

The second isolator 116 outputs the second beam to the beam interference unit 120 and blocks out incoming light from the beam interference unit 120.

The beam interference unit 120 divides the second beam into two beams. The port of one second beam divided by the beam interference unit 120 receives a first output beam returning from the beam output unit 130. The other second beam divided by the beam interference unit 120 is reflected from a reference reflector to generate a reflection beam. The beam interference unit 120 generates interference signal between the first output beam and the reflection beam to output the interference signal to the interference signal collection unit 140.

The beam interference unit 120 includes a beam divider 121, a polarizing controller 122, a second lens 123, a reference reflector 124 and a third lens 125.

The beam divider 121 divides the second beam that enters through a first path P1 into two beams. The beam divider 121 outputs one of the two divided second beams to the polarizing controller 122 through a second path P2 and outputs the other of the two divided second beams to the third lens 125 through a third path P3.

The beam divider 121 interferes in a reflection beam that enters through the second path P2 and a first output beam that enters through the third path P3. The beam divider 121 outputs the interfered beam to the interference signal collection unit 140 through a fourth path P4. At this time, the interfered beam does not enter the second light source 115 due to the second isolator 116 located at the first path P1.

The polarization controller 122 controls a polarization of the second beam that entered to output the polarization controlled second beam to the second lens 123. The polarization controller 122 outputs a reflection signal being output from the second lens 123 to the beam divider 121.

The second lens 123 controls the divided second beam to output the controlled second beam to the reference reflector 124. The second lens 123 output the refection signal reflected by the reference reflector 124 to the polarization controller 122.

The reference reflector 124 reflects the second beam to generate a reflection beam. The reference reflector 124 outputs the generated reflection beam to the second lens 123.

The third lens 125 receives and controls the other divided second beam to output it to the beam output unit 130. The third lens 125 outputs a signal being reflected from an eye to the beam divider 121.

The beam output unit 130 mixes the first and second beams generated through the beam generation unit 110 to make the mixed beam enter an anterior chamber of the eye 10 in a first direction. The beam output unit 130 receives a first output beam returning from the first direction.

The beam output unit 130 includes a reflector 131, a scanner 132 and a fourth lens 133.

The reflector 131 receives the first beam from the beam generation unit 110 and receives the divided second beam through the beam interference unit 120. The reflector 131 output the mixed first and second beam to the scanner 132. A dichroic mirror having a characteristic of transmitting the first beam and reflecting the second beam is used as the reflector 131.

The reflector 131 reflects a second beam being delivered from the scanner 132 so that the second beam is output to the beam interference unit 120.

The scanner 132 makes the mixed beam enter an anterior chamber of the eye 10 in the first direction. The scanner 132 is used to obtain a tomographic image. The scanner 132 can control an output direction of the mixed beam and can include a scanning device for controlling an output direction of the mixed beam. The scanner 132 outputs the mixed beam to the fourth lens 133.

The scanner 132 outputs a first output beam from the fourth lens 133 to the reflector 131.

The fourth lens 133 focuses the mixed beam into one point to output the focused mixed beam to an anterior chamber of the eye 10.

The fourth lens 133 transmits the first output beam corresponding to an output of the second beam to the scanner 132. The first output beam is an output beam returning from the anterior chamber of the eye 10.

The interference signal collection unit 140 collects an interference signal according to an interference of the beam interference unit 120.

The interference signal collection unit 140 includes an optical detector 141 and a data collector 142.

The optical detector 141 detects an interference signal through an interference of the reflection beam and the first output beam. The optical detector 141 outputs the detected interference signal to the data collector 142.

The data collector 142 collects an interference signal. The interference signal collected in the data collector 142 includes an interference light intensity of a light reflected from an anterior chamber of the eye 10 near a focus of the fourth lens 133.

The data collector 142 receives an interference signal and can obtain an interference light intensity on an optical path through an anterior chamber of the eye 10 using the interference signal. The data collector 142 outputs information about the obtained interference light intensity to the concentration measurement unit 160.

The optical activity measurement unit 150 receives a second output beam being output through the eye 10 to measure the rotation amount of a polarization plane.

The optical activity measurement unit 150 includes a fifth lens 151, a polarization analyzer 152 and a detection module 153.

The fifth lens 151 receives the second output beam being output through the eye 10. The second output beam is output at a specific angle to the first direction in which the mixed beam enters a lens of the eye 10. The fifth lens 151 outputs the second output beam to the polarization analyzer 152.

The polarization analyzer 152 may include a polarizer for a polarization analysis. The polarization analyzer 152 outputs the second output beam to the detection module 153 to extract a polarization component included in the second output beam.

The detection module 153 measures a light output from the polarization analyzer and calculates the rotation amount of polarization plane using a ratio of a direct current (DC) component and an alternating current (AC) component of the measurement value.

The polarization analyzer 152 and the detection module 153 measure the rotation amount of a polarization plane by comparing the polarization component of the second output beam with the polarization component applied to the first beam.

The polarization analyzer 152 and the detection module 153 including a process for removing birefringence of a cornea 15 and polarization effect by reflection on the surface of a lens 13 can measure a rotation angle of a polarization plane by aqueous humor using a comparison result between the polarization components. A cornea 15 of the eye 10 is a medium having birefringence and makes a linear polarization become an elliptical polarization. A change of polarization may occur by a reflection. The polarization analyzer 152 can analyze elliptical polarization components.

The optical activity measurement unit 150 outputs the rotation amount of a polarization plane to the concentration measurement unit 160.

The concentration measurement unit 160 measures a length of a path through which the mixed beam passes the eye 10 using the interference light intensity information. The concentration measurement unit 160 can calculate a glucose concentration of the eye 10 using the measured length and the rotation amount of a polarization plane. The concentration measurement unit 160 can store a table including glucose concentration information corresponding to the length information and the optical activity therein. The concentration measurement unit 160 can output the measured glucose concentration through a display unit.

The measuring device 100 can further include an aiming beam generator 170. The aiming beam generator 170 generates an aiming beam to easily aim a location and an angle of a lens 13 reflection surface of the eye 10. The aiming beam generator 170 can be located in front of the eye 10 and can be located between the beam output unit 130 and the optical activity measurement unit 150.

In the case that the first light source 111 and the second light source 115 of the beam generation unit 110 in the measuring device 100 are constituted by one beam generator, a polarizer can be used instead of the reflector 131. At this time, the measuring device 100 does not need the first lens 112 and the reflector 131.

The measuring device 100 measures an optical path length of the eye 10 and the rotation amount of a polarization plane at the same time using a non-invasive method to obtain a glucose concentration. Thus, the measuring device 100 can measure glucose concentration of the eye 10 regardless of an individual difference in a structure and size of the eye 10 and an effect caused by a movement of the eye 10 due to a heartbeat or a breath that may occur during a measurement to measure a glucose concentration.

Figure 2:
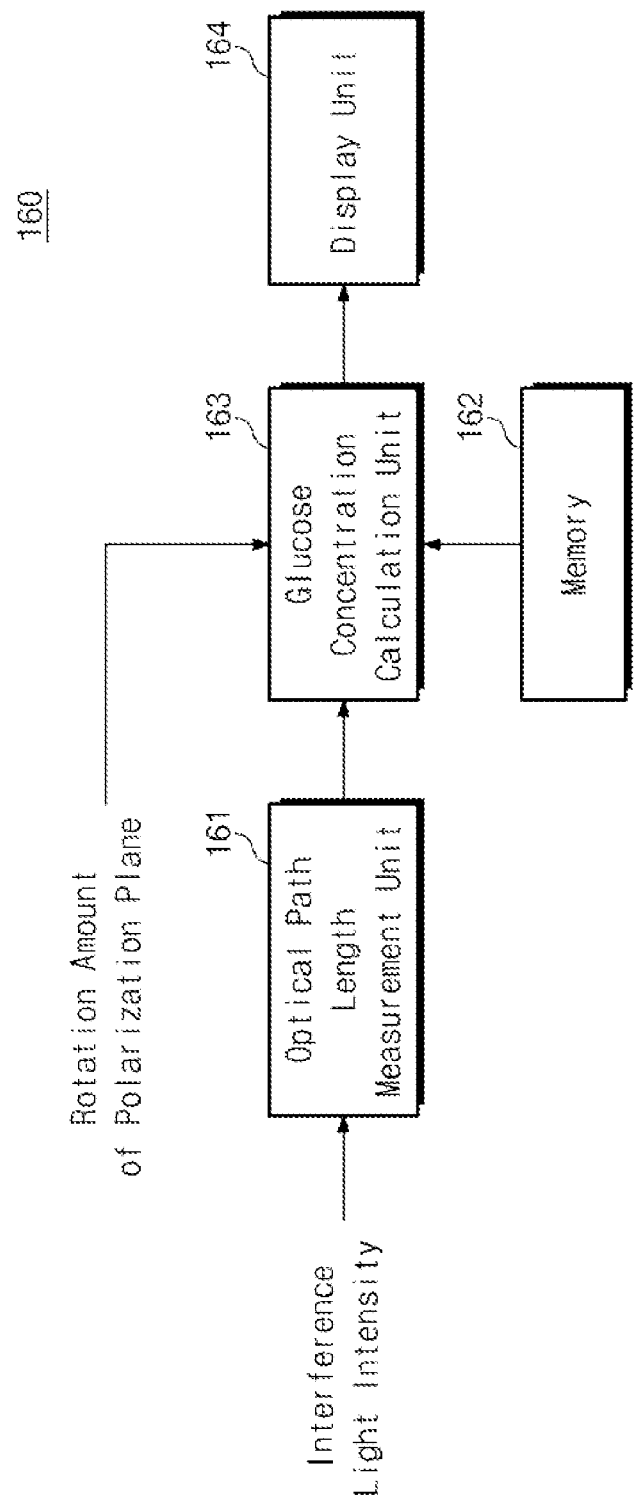
FIG. 2 is a drawing illustrating a structure of a concentration measurement unit according to some exemplary embodiments of the inventive concept.

FIG. 2 is a drawing illustrating a structure of a concentration measurement unit according to some exemplary embodiments of the inventive concept.

Referring to FIG. 2, the concentration measurement unit 160 includes an optical path length measurement unit 161, a memory 162, a glucose concentration calculation unit 163 and a display unit 164.

The optical path length measurement unit 161 receives interference light intensity distribution. The interference light intensity distribution includes length information that a light entering through the eye 10 travels until it is output. The optical path length measurement unit 161 can obtain a tomographic image using the interference light intensity distribution and can measure an optical path length using the tomographic image. The optical path length measurement unit 161 outputs the measured optical path length to the glucose concentration calculation unit 163.

The optical path length measurement unit 161 can use an algorithm for obtaining and analyzing an A-scanning signal and tomographic image to obtain a net path length of the mixed beam being reflected from an anterior chamber of the eye 10.

The optical path length measurement unit 161 extracts a optical path length between reflection surfaces. It allows the optical path length measurement unit 161 to estimate a vertical component of the optical path length that is a net optical path length.

The memory 162 stores a look-up table including glucose concentration information corresponding to the net optical path length and the rotation amount of a polarization plane.

The glucose concentration calculation unit 163 loads the look-up table stored in the memory to measure a glucose concentration from the rotation amount of a polarization plane and the net optical path length. The glucose concentration calculation unit 163 can obtain a glucose concentration from the glucose concentration of the look-up table corresponding to the optical path length and the rotation amount of a polarization plane. The glucose concentration calculation unit 163 outputs the calculated glucose concentration to the display unit 164.

The display unit 164 outputs a glucose concentration through a display screen. The display unit 164 can be constituted by various display devices for outputting image data.

Figure 3:
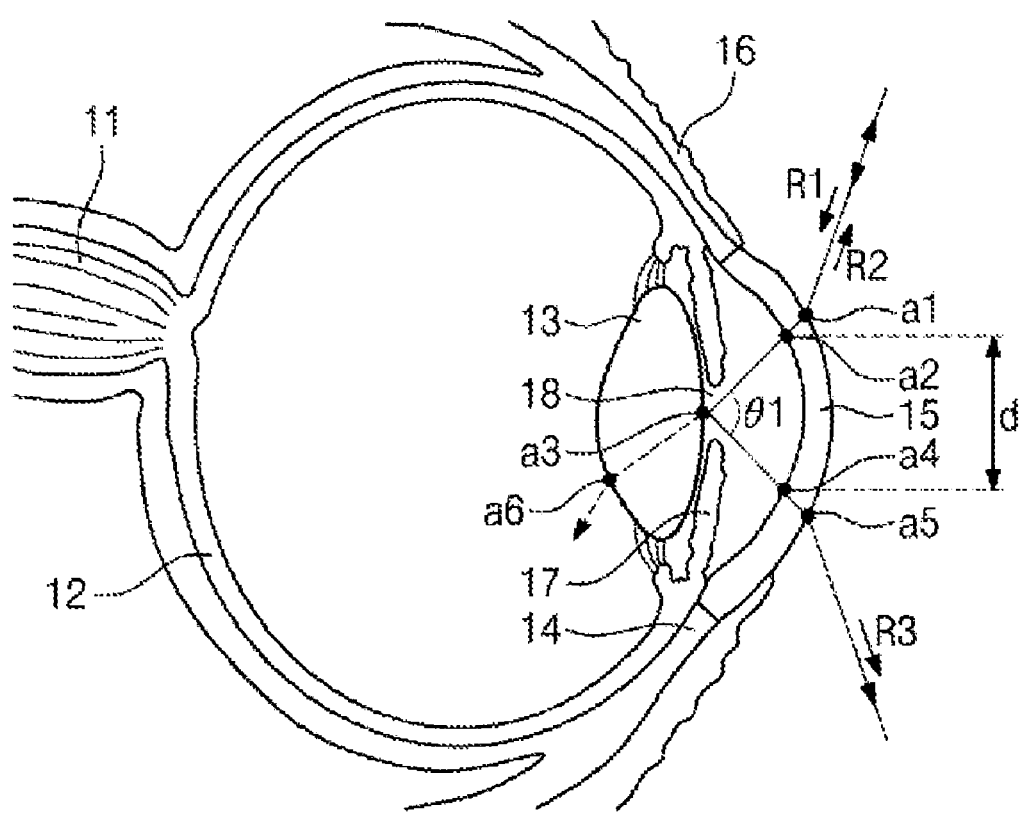
FIG. 3 is a drawing illustrating an operation such that a beam enters an eye and gets out of an eye according to some exemplary embodiments of the inventive concept.

FIG. 3 is a drawing illustrating an operation such that a beam enters an eye and gets out of an eye according to some exemplary embodiments of the inventive concept.

Referring to FIG. 3, the eye 10 includes an optic nerve 11, a retina 12, a lens 13, a sclera 14, a cornea 15, a conjunctiva 16, a iris 17 and a pupil 18.

The measuring device 100 measures a glucose concentration of an aqueous humor contained in an anterior chamber between the cornea 15 and the lens 13.

To achieve this, the beam output unit 130 of the measuring device 100 outputs the mixed beam obtained by mixing the first and second beams to the lens 13 through the cornea 15 in the first direction. At this time, when the mixed beam passes through the cornea 15, the mixed beam may be refracted.

The beam output unit 130 receives the first output beam returning from the first direction by outputting the mixed beam. A direction of outputting the mixed beam from the beam output unit 130 is represented by an arrow R1 and a direction of inputting the first output beam to the beam output unit 130 is represented by an arrow R2.

The optical activity measurement unit 150 receives the second output beam from a second direction having a specific angle θ1 to the first direction on the basis of the lens 13. The optical activity measurement unit 150 measures the rotation amount of a polarization plane from the second output beam. The first output beam and the second output beam are output in a different direction by the specific angle θ1.

An input direction of receiving the second output beam in the optical activity measurement unit 150 is represented by an arrow R3.

A net optical path length, distance d, measured in the optical path length measurement unit 161 is illustrated.

The points a1, a2, a3, a4 and a5 are shown at boundary points between the beam and the eye along a direction in which the mixed beam is input and a direction in which the second output beam is output. The points a1, a2, a3, a4 and a5 are crossing points on the cornea 15 and the lens 13 on an optical path. An optical path length can be measured according to an interference signal being occurred at the interfaces a1, a2, a3, a4 and a5.

A part of the mixed beam can pass through the lens 13 on the basis of a direction in which the mixed beam is input and a crossing point R6 of when passing through the lens 13 is shown.

Figure 4A:
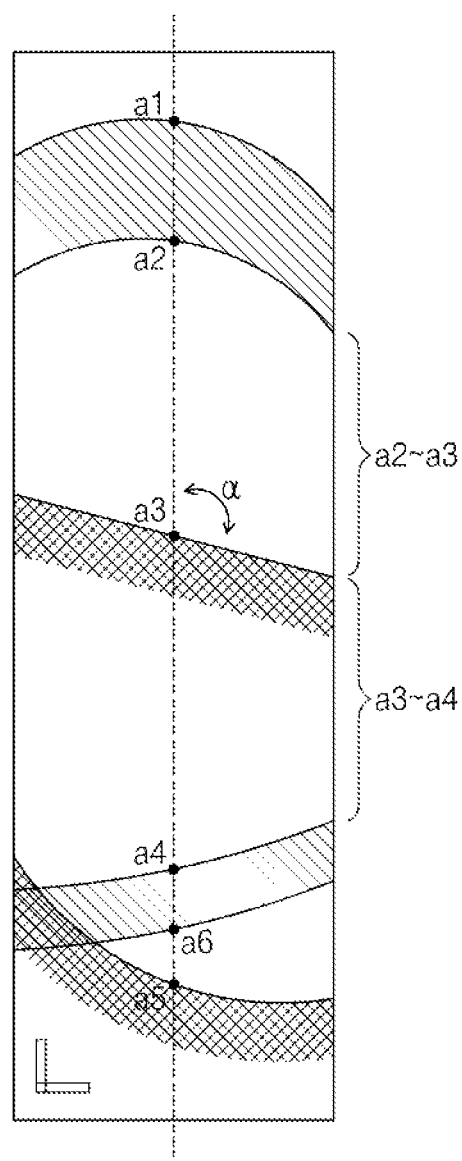
FIG. 4A is a drawing illustrating an optical tomography image (B scan) of an eye according to some exemplary embodiments of the inventive concept.

FIG. 4A is a drawing illustrating an optical tomographic image (B scan) of an eye according to some exemplary embodiments of the inventive concept.

Referring to FIG. 4A, the optical path length measurement unit 161 can check an angle with respect to an incident direction of each boundary surface of the eye 10. For example, a surface of the lens 13 is at the angle α with respect to an incident direction. In the case that a scale of a vertical axis and a scale of a horizontal axis are identical, the represented angle α is $$\alpha = 90° + \frac{\theta 1}{2}.$$

Figure 4B:
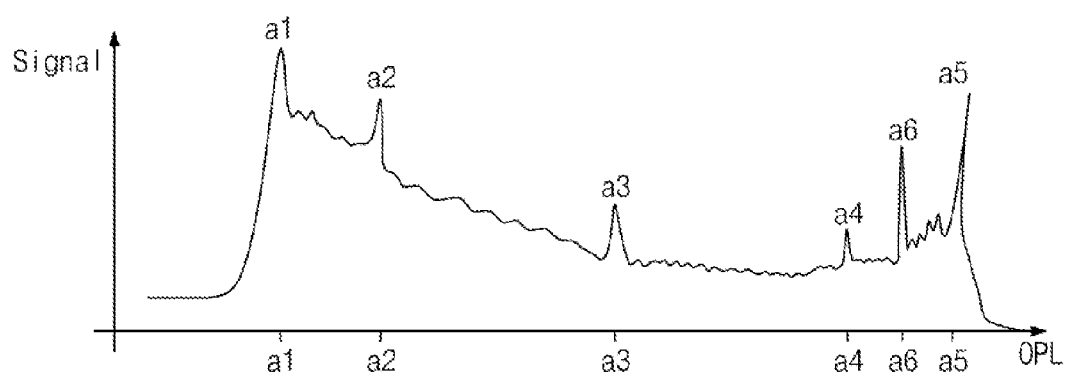
FIG. 4B is a drawing illustrating an optical interference tomography signal (A scan) of an eye according to some exemplary embodiments of the inventive concept.

FIG. 4B is a drawing illustrating an optical coherence tomography signal (A scan) of an eye according to some exemplary embodiments of the inventive concept.

Referring to FIG. 4B, the optical path length measurement unit 161 can obtain an optical coherence tomography signal (A scan) from a dotted line which is a part of the optical tomography image (B scan) of FIG. 4A. A horizontal axis of a graph represents an optical path length (OPL) and a vertical axis represents a signal intensity. In the concentration measurement unit 160, optical spectra including interference signals can be measured. The optical path length measurement unit 161 obtains an interference signal (e.g., a peak value) from the points a1, a2, a3, a4 and a5 on a path through which the mixed beam passes.

An optical path length between the first point a1 and the second point a2 is the product of a distance that the mixed beam passes through the cornea 15 and an average refractive index of the cornea 15. An optical path length between the second point a2 and the third point a3 is the product of a distance that the mixed beam which passed through the cornea 15 travels until it reaches a surface of the lens 13 and a refractive index of aqueous humor. An optical path length between the third point a3 and the fourth point a4 is the product of a distance that the mixed beam reflected from a surface of the lens 13 travels until it reaches the cornea 15 and a refractive index of aqueous humor. An optical path length between the fourth point a4 and the fifth point a5 is the product of a distance that the mixed beam passes through the cornea 15 and an average refractive index of the cornea 15.

The concentration measurement unit 160 can check a boundary surface on a path through which the mixed beam is reflected and output from the lens 13 using optical spectra including an interference signal. Through an analysis (e.g., Fourier transform) of a spectrum, the concentration measurement unit 160 can measure a path length through which the mixed beam passes as illustrated in FIGS. 4A and 4B.

A net optical path length, that is distance d, can be calculated from an incident angle $$\frac{\theta 1}{2},$$

refractive index of aqueous humor, and an optical path length (e.g., a distance between a2 and a3) which are obtained from FIGS. 4A and 4B.

Figure 5:
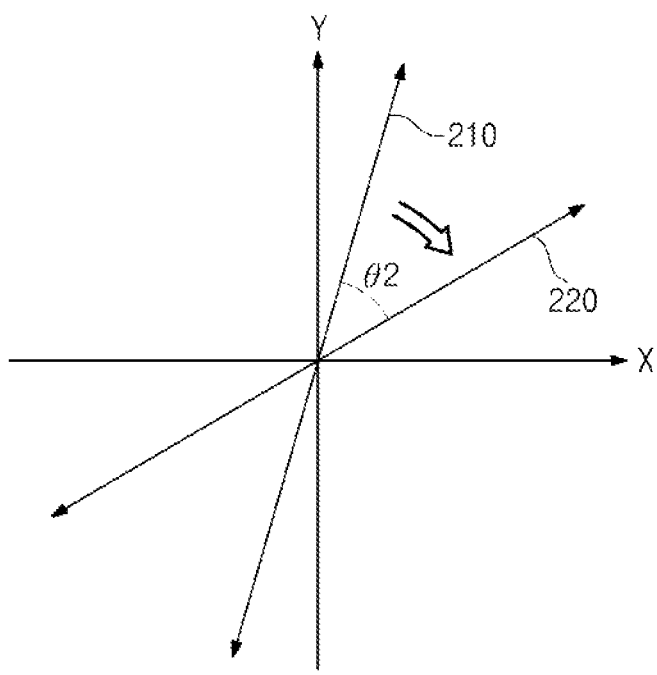
FIG. 5 is a drawing illustrating the rotation of a polarization plane according to some exemplary embodiments of the inventive concept.

FIG. 5 is a drawing illustrating a polarization rotation for measuring the rotation amount of a polarization plane according to some exemplary embodiments of the inventive concept.

Referring to FIG. 5, the rotation amount of a polarization plane can be measured by a polarization component included a beam that entered the eye 10 and a beam being output from the eye 10. To achieve this, a polarization characteristic is illustrated on the basis of a horizontal axis (x axis) and a vertical axis (y axis).

A first polarization component 210 of the first beam and a second polarization component 220 of the second beam are illustrated. If the first beam passes through aqueous humor of the eye 10, the first polarization component 210 is changed by θ2. The rotation of the first polarization component 210 is due to a glucose component of the aqueous humor.

The optical activity measurement unit 150 can measure the rotation amount of a polarization plane by the rotation θ2 of a linear polarization due to the first polarization component 210 and the second polarization component 220.

The measuring device 100 of the inventive concept can be used to non-invasively measure a glucose concentration of an aqueous humor in an actively moving eye of human or animal. The measuring device 100 can obtain a glucose concentration in real time by measuring a net optical path length and the rotation amount of a polarization plane at the same time.

To measure optical activity, a zero point of the rotation amount of a polarization plane can be obtained from the measuring device 100. A linear polarization rotation zero point can be calibrated by placing a reflection surface on the location at which a surface of the lens 13 of the eye 10 is placed and by referring an aiming beam of the aiming beam generator 170. Thus, the rotation of a polarization plane can be accurately measured.

The measuring device of the inventive concept can non-invasively and accurately measure a glucose concentration of aqueous humor by controlling so that a beam is reflected at a specific angle in an eye to measure a path length of a beam in real time and by measuring a rotation of a polarization plane of a light passing through a medium at the same time.

The above-disclosed subject matter is to be considered illustrative, and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:

1. A method of measuring a glucose concentration of a measuring device comprising:
    generating a first beam including polarizing components, which are applied by a polarizer;
    generating a second beam which is a wavelength swept laser beam having a coherence length previously set;
    sending a mixed beam obtained by mixing the first and second beams to an eye in a first direction;
    measuring a net optical path length by interference between a reflection beam which is reflected from a reference reflector and a first output beam being output returning from the eye in a first direction, wherein the measuring the net optical path length comprises:
        generating an interference beam by interference between the first output beam and the reflection beam;
        measuring an angle of a surface of the lens with respect to an in incident direction using an optical coherence tomography signal included in the interference beam; and
        estimating the net optical path length using the angle and at least one of optical path length between reflection surfaces;
    measuring the rotation amount of a polarization plane from a second output beam being output in a second direction having a specific angle with respect to the first direction; and
    measuring a glucose concentration of an aqueous humor on the basis of the net optical path length and the rotation amount of the polarization plane.

2. The method of measuring a glucose concentration of claim 1, wherein the measuring the rotation amount of a polarization plane comprises:
    measuring a change of a polarization component by comparing a polarization component included in the first beam with a polarization component included in the second output beam; and
    measuring the rotation amount of the polarization plane through the change of the polarization component.

3. The method of measuring the rotation amount of a polarization plane of claim 2, wherein measuring the change of the polarization component comprises:
    applying a linear polarization in the first beam using the polarizer;
    measuring a polarization plane of a linear polarization included in the second output beam using an optical activity measurement unit; and
    comparing the polarization plane in the second output beam with a polarization plane in the first beam.

4. The method of measuring a glucose concentration of claim 1, wherein the measuring the glucose concentration includes determining a glucose concentration from a look-up table of a glucose concentration on the basis of the net optical path length and the rotation amount of the polarization plane.

5. The method of measuring a glucose concentration of claim 1, further comprising displaying the measured glucose concentration through a display device.

6. The method of measuring a net optical path length of claim 1, wherein measuring the angle of a surface of the lens with respect to an incident direction comprises measuring an optical coherence tomographic image of the lens surface using a scanner.

7. The method of measuring a net optical path length of claim 1, wherein generating the interference beam by interference between the first output beam and the reflection beam comprises:
    sending the second beam through a beam output unit to the eye; and receiving the first output beam returning from the eye through the beam output unit.

* * * * *